(12) United States Patent
Marchionni et al.

(10) Patent No.: US 8,946,136 B2
(45) Date of Patent: Feb. 3, 2015

(54) HYDROFLUOROALCOHOLS WITH IMPROVED THERMAL AND CHEMICAL STABILITY

(75) Inventors: Giuseppe Marchionni, Milan (IT); Ugo De Patto, Cogliate Milan (IT); Marco Avataneo, Milan (IT)

(73) Assignee: Solvay Specialty Polymers Italy S.p.A., Bollate (IT)

( * ) Notice: Subject to any disclaimer, the term of this patent is extended or adjusted under 35 U.S.C. 154(b) by 661 days.

(21) Appl. No.: 13/058,297

(22) PCT Filed: Aug. 7, 2009

(86) PCT No.: PCT/EP2009/060302
§ 371 (c)(1),
(2), (4) Date: Feb. 9, 2011

(87) PCT Pub. No.: WO2010/057691
PCT Pub. Date: May 27, 2010

(65) Prior Publication Data
US 2011/0136713 A1 Jun. 9, 2011

(30) Foreign Application Priority Data
Aug. 11, 2008 (EP) .................................. 08425563

(51) Int. Cl.
| | | |
|---|---|---|
| C10M 147/04 | (2006.01) | |
| C07C 43/13 | (2006.01) | |
| C07C 41/01 | (2006.01) | |
| C07C 41/42 | (2006.01) | |
| C07C 43/313 | (2006.01) | |
| C07C 69/653 | (2006.01) | |
| C07C 319/08 | (2006.01) | |

(52) U.S. Cl.
CPC ............... *C07C 43/137* (2013.01); *C07C 41/01* (2013.01); *C07C 41/42* (2013.01); *C07C 43/313* (2013.01); *C07C 69/653* (2013.01); *C07C 319/08* (2013.01); *C10M 147/04* (2013.01); *C10M 2213/04* (2013.01); *C10M 2213/0606* (2013.01); *C10N 2230/06* (2013.01); *C10N 2230/12* (2013.01); *C10N 2240/205* (2013.01); *C10N 2250/10* (2013.01)
USPC ............................ 508/582; 508/583; 508/579

(58) Field of Classification Search
USPC .......................................... 508/579, 582, 583
See application file for complete search history.

(56) References Cited

U.S. PATENT DOCUMENTS

| | | | |
|---|---|---|---|
| 2,519,983 | A | 8/1950 | Simons |
| 3,242,218 | A | 3/1966 | Miller |
| 3,362,980 | A | 1/1968 | Christe et al. |
| 3,810,874 | A | 5/1974 | Mitsch et al. |
| 3,847,978 | A | 11/1974 | Sianesi et al. |
| 4,551,448 | A | 11/1985 | Seufert et al. |
| 4,721,795 | A | 1/1988 | Caporiccio et al. |
| 4,757,145 | A | 7/1988 | Caporiccio et al. |
| 4,853,097 | A | 8/1989 | Marchionni et al. |
| 5,104,559 | A | 4/1992 | Pawloski et al. |
| 5,466,877 | A | 11/1995 | Moore |
| 5,936,102 | A | 8/1999 | Popkova et al. |
| 6,127,498 | A | 10/2000 | Tonelli et al. |
| 7,138,551 | B2 | 11/2006 | Shtarov et al. |
| 7,285,231 | B2 | 10/2007 | Weippert |
| 2001/0034301 | A1* | 10/2001 | Hanada et al. ............... 503/227 |
| 2004/0147780 | A1 | 7/2004 | Fontana et al. |
| 2005/0192413 | A1 | 9/2005 | Marchionni et al. |
| 2006/0287559 | A1 | 12/2006 | Friesen et al. |

FOREIGN PATENT DOCUMENTS

| | | | |
|---|---|---|---|
| CN | 1371927 | A | 10/2002 |
| EP | 0091598 | A2 | 10/1983 |
| EP | 0273409 | A1 | 7/1988 |
| EP | 0368008 | A1 | 5/1990 |
| EP | 0391390 | A1 | 10/1990 |
| EP | 0893444 | A1 | 1/1999 |
| EP | 1136278 | A1 | 9/2001 |
| EP | 1522536 | A1 | 4/2005 |
| EP | WO 2007075804 | A1 | 7/2007 |
| JP | 61-257226 | A | 11/1986 |
| JP | 2-167375 | A | 6/1990 |
| JP | 7-133253 | A | 5/1995 |

(Continued)

OTHER PUBLICATIONS

Tonelli, C., et al—"Linear perfluoropolyether difunctional oligomers: chemistry, properties and applications", 1999, Journal of Fluorine Chemistry, vol. 95, Elsevier Science SA, pp. 51-70; 20 pgs.

Scicchitano, Massimo, et al—"Synthesis and characterization of low-viscosity fluoropolyether-based segmented oligomers", 1995, Die Angewandte Makromoleculare Chemie, vol. 231, Issue No. 4000, Hüthig & Wepf Verlag, Zug, pp. 47-60; 14 pgs.

Cherbukov, Y., et al—"Perfluoroalcohols", 2002, Journal of Fluorine Chemistry, vol. 118, Elsevier Science BV, pp. 123-126; 4 pgs.

Aldrich, P.E., et al—"α-Fluorinated Ethers. II. Alkyl Fluoroalkyl Ethers", 1964, Journal of Organic Chemistry, vol. 29, pp. 11-15; 5 pgs.

Vogel, A.I.—"Butyl Toluene-p-Sulphonate", 1978, Vogel's Textbook of Practical Organic Chemistry, 4th edition, revised by Furniss et al., Ed. Longman, London and New York, pp. 654-655,; 3 pgs.

(Continued)

*Primary Examiner* — Sudhakar Katakam
*Assistant Examiner* — Pancham Bakshi
(74) *Attorney, Agent, or Firm* — Arent Fox LLP

(57) ABSTRACT

Hydrofluoro alcohols of formula (I): $A\text{-}(R_f)_a\text{—}CFX\text{—}O\text{—}R_hO\text{—}(CFX\text{—}(R_f)_{a^*}\text{—}CFX\text{—}O\text{—}R_hO\text{—})_nH$ in which: $R_h$ is a hydrocarbon-based chain; X is F or a $C_1$-$C_6$ (per)fluoroalkyl; a or a* is 0 or 1; $R_f$ is a (per)fluoro(poly)oxyalkylene chain or a (per)fluoroalkyl chain; A is selected from the group consisting of —F, —Cl, and —H (possible only when a=1) or is HO—$R_h$—O—CFX—; n is an integer from 0 to 200, with the condition that n=0 when A is selected from the group consisting of —F, —Cl, and —H.

9 Claims, No Drawings

(56) References Cited

FOREIGN PATENT DOCUMENTS

| JP | 10-087526 A | 4/1998 |
|---|---|---|
| JP | 10-091936 A | 4/1998 |

OTHER PUBLICATIONS

March, J.—"Reactions, Mechanisms and Structure", 2001, March's Advanced Organic Chemistry, 5th Edition, pp. 482-485, 493-494, 576, 1180-1183, Wiley-Interscience Publication, John Wiley & Sons, Inc.; 16 pgs.

Zuev, V.V., "Liquid-crystalline multiblock copolymers based on perfluoroethylene oxides", 2006, Vysokomolekulyarnye Soedineniya, Seriya A| Seriya B, vol. 48, Issue No. 7, pp. 1195-1197, and ISSN 1560-0904 Polymer Science Ser. B, Pleiades Publishing, Inc., CAS 145:505880—XP002568884; 5 pgs.

Lichtenberger, J.—"Nucleophilic additions to trfluorochloroethylene", Bulletin de la Société Chimique de France, 1962, pp. 325-329—XP009136709 ; 6 pgs.

Uno, H., et al—"Perfluoroalkyl Migration in the Rearrangement of 4-Perfluoroalkyl-4-quinols", 1992, Tetrahedron, vol. 48, Issue No. 39, pp. 8353-8368—XP002593285; 16 pgs.

Julia, M., et al—"Prenylation of isopentenyl derivatives with 2-methyl-3-buten-2-ol", 1986, Bulletin de la Société Chimique de France, vol. 4, pp. 630-636—XP009136604 ; 7 pgs.

\* cited by examiner

HYDROFLUOROALCOHOLS WITH IMPROVED THERMAL AND CHEMICAL STABILITY

CROSS-REFERENCE TO RELATED APPLICATIONS

This application is a U.S. national stage application under 35 U.S.C. §371 of International Application No. PCT/EP2009/060302 filed Aug. 7, 2009, which claims priority to European Application No. 08425563.7 filed Aug. 11, 2008, these applications being herein incorporated by reference in their entirety for all purposes.

The present invention relates to hydrofluoro alcohols with improved chemical stability, in particular to acids and bases, in combination with better thermal stability, and to the process for preparing them.

More specifically, the invention relates to hydrofluoro alcohols in which the fluorinated part is perfluoropolyether-based or perfluoroalkyl-based, with improved stability to Brönsted acids and Lewis acids.

It is known in the art that hydrofluoro alcohols are compounds characterized by a low vapour pressure and low surface tension values. In addition, hydrofluoropolyether alcohols, for example the products known as Fomblin® Z-DOL and Fomblin® Z-DOL TX, sold by Solvay Solexis, also show low glass transition (Tg) values. The presence of alcohol functions allows the preparation of derivatives with various functionalities, for example of ester type.

Hydrofluoro alcohols and derivatives thereof find an application in the treatment of surfaces, such as glass, cardboard and textiles, as surfactants, as lubrication additives, as additives for modifying the surface properties of polymer materials, as magnetic lubricants, and as liquids for immersion microscopy. In particular, hydrofluoro alcohols with two or more alcohol groups per molecule (functionality of greater than or equal to two) may be used as macromers ("building blocks") for the synthesis or crosslinking of polymer materials.

Commercial hydrofluoro alcohols having perfluoropolyether or perfluoroalkyl structures generally have end groups of the type —$CF_2(CH_2)_bOH$ in which b=1 or 2. For example, hydrofluoro alcohols of perfluoropolyether structure, such as those known as Fomblin® Z-DOL, have b=1. Alcohols of perfluoroalkyl structure, such as Zonyl® BA Fluoroalcohol, have b=2.

Hydrofluoro alcohols may be converted into the corresponding esters, for example phosphates, by reaction with $POCl_3$. However, the esters thus obtained from alcohols with —$CF_2CH_2OH$ end groups (b=1) are readily hydrolysed. See, for example, the report given in C. Tonelli et al., Journal of Fluorine Chemistry, 95 (1999), page 53. In order to obtain esters with improved hydrolytic stability, the hydrofluoro alcohols with —$CF_2CH_2OH$ end groups are converted into alcohol derivatives in which the OH group is further removed from the fluoro chain. This may be performed, for example, using reactions with ethylene oxide, as described in M. Scicchitano et al., Die. Ang. Makromol. Chem., 231 (1995) 47-60. In this case, reaction with ethylene oxide gives —$CF_2CH_2$—$O(CH_2CH_2O)_cH$ end groups with c between 1 and 1.5. In this way, the derivatives have improved hydrolytic stability. However, the product obtained contains hydrogenated ether bonds —$CH_2OCH_2$— that are liable to undergo chemical attack, in particular by acids.

It is also known that alcohols with —$CF_2(CH_2)_2OH$ end groups and derivatives thereof undergo dehydro fluorination reactions of the —$CF_2CH_2$— group as reported, for example, in U.S. Pat. No. 7,138,551. This generally occurs in the presence of bases and/or at high temperatures, for example using an aqueous KOH solution at 10% by weight at 90° C. or by heating to high temperatures, for example above 175° C. See Scicchitano (ib.) and the tests performed by the Applicant (comparative examples).

Hydrofluoro alcohols having the perfluoroalkyl perfluoropolyether structure in which the end group is —$R_fCH_2(C_qH_{2q})OH$ where q=1-10 are also known. See, for example, US 2006/287 559. The ester derivatives obtained therefrom show improved hydrolytic stability. However, the alcohols having this structure and derivatives thereof have the drawback of having low chemical resistance to bases and/or to high temperatures and have little thermal resistance, like the compounds described above in which b=2.

There was thus felt to be a need for hydrofluoro alcohols having the following combination of properties:
- improved chemical resistance to acids and bases, in particular to Brönsted acids and Lewis acids,
- improved thermal stability at high temperatures of the order of 180° C., and even greater than 210° C.,
- improved hydrolytic stability of the hydrofluoro alcohol derivatives, in particular derivatives of ester type.

The Applicant has found, surprisingly and unexpectedly, particular hydrofluoro alcohols that solve the described technical problem.

One subject of the present invention is hydrofluoro alcohols of formula:

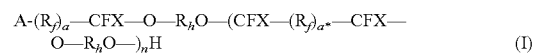

$$A-(R_f)_a-CFX-O-R_hO-(CFX-(R_f)_{a^*}-CFX-O-R_hO-)_nH \quad (I)$$

in which:

$R_h$ is a divalent $C_1$-$C_{20}$ hydrocarbon-based residue,

X is F or a $C_1$-$C_6$ (per)fluoroalkyl, which is linear or branched where possible, optionally containing one or more heteroatoms, a and a*, equal to or different from each other and at each occurrence, are independently an integer equal to 0 or 1, $R_f$ is a (per)fluoro(poly)oxyalkylene (PFPE) chain or a (per)fluoroalkyl chain, A is selected from:
- a group of formula: HO—$R_h$—O—CFX— in which $R_h$ and X are as defined, and
- a group selected from —F, —Cl and —H, with the provisio that A can be a group selected from —F, —Cl and —H only when a=1;

n is an integer from 0 to 200, with the condition that n=0 when A is chosen from —F, —Cl and —H.

Preferably $R_h$ is chosen from:
- a $C_1$-$C_{10}$ alkyl chain, which is linear or branched where possible,
- a $C_3$-$C_{10}$ cyclic ring or a $C_4$-$C_{20}$ alkyl chain comprising one or more $C_3$-$C_{10}$ cyclic rings,
- an aromatic ring in which, optionally, one or more carbon atoms of the said aromatic ring are substituted with a heteroatom, or a $C_6$-$C_{20}$ alkyl chain comprising one or more of the said aromatic rings, $R_h$ may contain one or more unsaturations; the cyclic and/or aromatic rings may have one or more hydrogen atoms replaced with $C_1$-$C_{10}$ (fluoro)alkyl chains, which are linear or branched where possible. $R_h$ is preferably an alkyl chain, which is linear or branched where possible, more preferably of $C_2$-$C_{10}$ and even more preferably of $C_2$-$C_6$, optionally containing one or more unsaturations. $R_h$ may optionally contain one or more heteroatoms, for instance non-ether oxygen, N, etc.

When X is a (per)fluoroalkyl group, the end group of the perfluoroalkyl group may contain one or more hydrogen atoms, preferably one hydrogen atom. When X contains one or more heteroatoms, it is preferably oxygen. When X is a perfluoroalkyl, it is preferably of $C_1$-$C_3$, which is linear or branched where possible. More preferably, X is F.

The indexes a and a* are preferably equal to 1.

The index n preferably ranges from 0 to 100 and more preferably between 0 and 50.

Preferably, $R_f$ is a PFPE chain having a number-average molecular weight from about 100 to about 10 000; when it is a (per)fluoroalkyl chain, it is preferably a $C_1$-$C_{30}$ (per)fluoroalkyl chain, which is a linear or branched, where possible.

The chain $R_f$ may contain one or more $C_3$-$C_{10}$ (per)fluorinated cyclic rings, optionally substituted with fluorine atoms or with one or more $C_1$-$C_{10}$ (per)fluoroalkyl chains, which are linear or branched where possible.

When $R_f$ is a perfluoroalkyl group, it is preferably a linear chain, more preferably of $C_1$-$C_8$. According to this embodiment, $R_f$ may optionally contain along the chain (backbone) one or more —CFYOR$_h$OH pendent groups, in which $R_h$ is as defined above, and Y is F or a $C_1$-$C_6$ (per)fluoroalkyl, which is linear or branched where possible. In this case, the compound of formula (I) contains several —OH groups. Preferably, the number of pendent groups ranges from 1 to 10. When —CFYOR$_h$OH pendent groups are present, n is preferably equal to 0.

When $R_f$ is a (per)fluoro(poly)oxyalkylene chain, it preferably has a molecular weight of between 116 and 3000. According to this embodiment, $R_f$ is preferably a (per)fluoro(poly)oxyalkylene chain comprising one or more of the following sequences statistically distributed along the chain: —($C_3F_6$O)—, —($CF_2$O)—, —($CF_2CF_2$O)—, —($CF_2CF_2CF_2$O)—, —($CF_2CF_2CF_2CF_2$O)—, —(CF(CF$_3$)O)—. Optionally, in $R_f$ of this embodiment may comprise units —($CF_2$CF(CFYOR$_h$OH)O)—, —(CF(CFYOR$_h$OH)CF$_2$O)— and —(CF(CFYOR$_h$OH)O)— with Y and $R_h$ as defined. The unit —($C_3F_6$O)— may be —($CF_2$CF(CF$_3$)O)— or —(CF(CF$_3$)CF$_2$O)—.

More preferably, $R_f$ according to this embodiment is chosen from the following fluoro(poly)oxyalkylene structures:

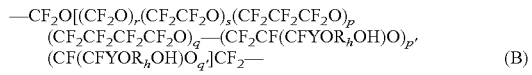

(B)

in which the indices r, s, p, q, p' and q' are integers, including zero, such that the number-average molecular weight is as indicated hereinabove; preferably, when r is other than zero, s/r is between 0.1 and 10; when (r+s) is other than zero, (p+q)/(r+s) is between 0 and 0.2, limits inclusive;

$R_h$ and Y are as defined,

(C)

in which the indices r, s, t, u, p' and q' are integers, including zero, such that the number-average molecular weight is as indicated; preferably, when s is other than zero, t/s is between 0.1 and 10; when (t+s) is other than zero, (r+u)/(t+s) is between 0.01 and 0.5 and more preferably between 0.01 and 0.2;

$R_h$ is as defined; Y, Y' and Y" are chosen from F and $C_1$-$C_6$ (per)fluoroalkyl, which are linear or branched where possible.

The compounds of formula (I) generally have a number-average molecular weight of between about 100 and 300 000, preferably between about 200 and 200 000, more preferably between about 400 and 50 000 and even more preferably between 600 and 10 000. In one particularly preferred embodiment, the number-average molecular weight is between 150 and 3000.

Examples of compounds of formula (I) are the following:

$CF_3(CF_2)_2OCH_2CH_2OH$
$CF_3(CF_2)_2OCH_2CH_2CH_2OH$
$CF_3(CF_2)_2OCH_2CH_2CH_2CH_2OH$
$CF_3(CF_2)_2OCH_2$-($cC_6$—$H_{10}$)—$CH_2OH$
$CF_3(CF_2)_2OCH_2$-Ph-$CH_2OH$ with Ph=$C_6H_4$
$CF_3(CF_2)_2OCH_2CH$=$CHCH_2OH$
$CF_3(CF_2)_3OCH_2CH_2OH$
$CF_3(CF_2)_3OCH_2CH_2CH_2OH$
$CF_3(CF_2)_3OCH_2CH_2CH_2CH_2OH$
$CF_3(CF_2)_5OCH_2CH_2CH_2CH_2OH$
$HOCH_2CH_2O$—$(CF_2)_6$—$OCH_2CH_2OH$
$HOCH_2CH_2CH_2O$—$(CF_2)_6$—$OCH_2CH_2CH_2OH$
$HOCH_2CH_2CH_2CH_2O$—$(CF_2)_6$—$OCH_2CH_2CH_2CH_2OH$
$HOCH_2CH_2O$—$(CF_2)_6$—$OCH_2CH_2O$—$[(CF_2)_6OCH_2CH_2O]_nH$
$HOCH_2CH_2CH_2O$—$(CF_2)_6$—$OCH_2CH_2CH_2O$—$[(CF_2)_6$—$OCH_2CH_2CH_2O$—$]_nH$
$HOCH_2CH_2CH_2O$—$(CF_2)_6$—$OCH_2CH_2CH_2CH_2O$—$[(CF_2)_6$—$OCH_2CH_2CH_2$—$CH_2O$—$]_nH$
$CF_3CF_2CF_2OCF(CF_3)CF_2OCH_2CH_2OH$
$CF_3CF_2CF_2OCF(CF_3)CF_2OCH_2CH_2CH_2OH$
$CF_3CF_2CF_2OCF(CF_3)CF_2OCH_2CH_2CH_2CH_2OH$
$CF_3CF_2CF_2OCF(CF_3)CF_2OCF(CF_3)$
$CF_2OCH_2CH_2CH_2CH_2OH$
$HCF_2OCF(CF_3)CF_2OCH_2CH_2OH$
$HCF_2OCF(CF_3)CF_2OCH_2CH_2CH_2OH$
$HCF_2OCF(CF_3)CF_2OCH_2CH_2CH_2CH_2OH$
$HCF_2OCF(CF_3)CF_2OCF(CF_3)CF_2OCH_2CH_2CH_2CH_2OH$
$HCF_2CF_2OCF(CF_3)CF_2OCH_2CH_2OH$
$HCF_2CF_2OCF(CF_3)CF_2OCH_2CH_2CH_2OH$
$HCF_2CF_2OCF(CF_3)CF_2OCH_2CH_2CH_2CH_2OH$
$HCF_2CF_2OCF(CF_3)CF_2OCF(CF_3)$
$CF_2OCH_2CH_2CH_2CH_2OH$
$HCF(CF_3)CF_2OCF(CF_3)CF_2OCH_2CH_2OH$
$HCF(CF_3)CF_2OCF(CF_3)CF_2OCH_2CH_2CH_2OH$
$HCF(CF_3)CF_2OCF(CF_3)CF_2OCH_2CH_2CH_2CH_2OH$
$HCF(CF_3)CF_2OCF(CF_3)CF_2OCF(CF_3)$
$CF_2OCH_2CH_2CH_2CH_2OH$
$ClCF(CF_3)CF_2OCF(CF_3)CF_2OCH_2CH_2OH$
$ClCF(CF_3)CF_2OCF(CF_3)CF_2OCH_2CH_2CH_2OH$
$ClCF(CF_3)CF_2OCF(CF_3)CF_2OCH_2CH_2CH_2CH_2OH$
$ClCF(CF_3)CF_2OCF(CF_3)CF_2OCF(CF_3)$
$CF_2OCH_2CH_2CH_2CH_2OH$
$CF_3OCF(CF_3)CF_2OCH_2CH_2OH$
$CF_3OCF(CF_3)CF_2OCH_2CH_2CH_2OH$
$CF_3OCF(CF_3)CF_2OCH_2CH_2CH_2CH_2OH$
$CF_3CF_2OCF(CF_3)CF_2OCH_2CH_2OH$
$CF_3CF_2OCF(CF_3)CF_2OCH_2CH_2CH_2OH$
$CF_3CF_2OCF(CF_3)CF_2OCH_2CH_2CH_2CH_2OH$
$(CF_3)_2CFOCF(CF_3)CF_2OCH_2CH_2OH$
$(CF_3)_2CFOCF(CF_3)CF_2OCH_2CH_2CH_2OH$
$(CF_3)_2CFOCF(CF_3)CF_2OCH_2CH_2CH_2CH_2OH$
F—$R_f$—$CF_2OCH_2CH_2OH$
F—$R_f$—$CF_2OCH_2CH_2CH_2OH$
F—$R_f$—$CF_2OCH_2CH_2CH_2CH_2OH$
F—$R_f$—$CF_2OCH_2$-($cC_6H_{10}$)—$CH_2OH$
F—$R_f$—$CF_2OCH_2$-Ph-$CH_2OH$ with Ph=$C_6H_4$
F—$R_f$—$CF_2OCH_2CH$=$CHCH_2OH$
$HOCH_2CH_2OCF_2$—$R_f$—$CF_2OCH_2CH_2OH$ HOCH$_2$CH$_2$CH$_2$OCF$_2$—R$_f$—CF$_2$OCH$_2$CH$_2$CH$_2$OH
HOCH$_2$CH$_2$CH$_2$CH$_2$OCF$_2$—R$_f$—
CF$_2$OCH$_2$CH$_2$CH$_2$CH$_2$OH
HOCH$_2$-(cC$_6$H$_{10}$)—CH$_2$—OCF$_2$—R$_f$—CF$_2$O—CH$_2$-(cC$_6$H$_{10}$)—CH$_2$OH
HOCH$_2$CH$_2$OCF$_2$—R$_f$—CF$_2$OCH$_2$CH$_2$O—(CF$_2$—R$_f$—CF$_2$OCH$_2$CH$_2$O—)$_n$H
HOCH$_2$CH$_2$CH$_2$OCF$_2$—R$_f$—CF$_2$OCH$_2$CH$_2$CH$_2$O—(CF$_2$—R$_f$—CF$_2$OCH$_2$CH$_2$CH$_2$O—)$_n$H
HOCH$_2$CH$_2$CH$_2$CH$_2$OCF$_2$—R$_f$—CF$_2$OCH$_2$CH$_2$CH$_2$CH$_2$O(CF$_2$—R$_f$—CF$_2$OCH$_2$CH$_2$CH$_2$CH$_2$O)$_n$H
HOCH$_2$-(cC$_6$H$_{10}$)—CH$_2$—OCF$_2$—R$_f$—CF$_2$O—CH$_2$-(cC$_6$H$_{10}$)—CH$_2$O—(CF$_2$—R$_f$—CF$_2$O—CH$_2$-(cC$_6$H$_{10}$)—CH$_2$—O)$_n$H.

In the illustrated compounds, the index n is an integer between 1 and 10, and may be pure products or mixtures of products of different n. R$_f$ in the illustrated formulae is a (per)fluoro(poly)oxyalkylene chain as above defined, preferably complying with formula:

$$—[CF_2O(CF_2O)_s(CF_2CF_2O)_r(CF_2CF_2CF_2O)_p(CF_2CF_2CF_2CF_2O)_qCF_2]—$$

wherein p, q, r, s are integers≥0, and wherein, when s is other than 0, the r/s ratio is preferably between 0.5 and 2.5, and wherein, when (r+s) is other than 0, the (p+q)/(r+s) ratio is preferably between 0 and 0.2, limits inclusive, the number-average molecular weight being generally between 200 and 1000.

The hydrofluoro alcohols of the present invention are, surprisingly and unexpectedly, particularly chemically stable to bases and acids, both Brönsted acids and Lewis acids, and also heat-stable. They do not show any dehydrofluorination reactions at high temperatures of about 180° C., or even above 210° C.

The compounds of formula (I) of the present invention may be prepared via a process comprising the following steps:

Step a)
reaction of a difunctional alkylating compound of formula:

$$B—O—R_h—O—B \quad (II)$$

in which:
R$_h$ is as defined above,
B is FC(O)—, R'—SO$_2$— in which is an aromatic group, a hydrogenated or
(per)fluorinated C$_1$-C$_{10}$ alkyl, which is linear or branched where possible, with
a carbonyl compound of formula:

$$A'—(R_f)_a—COX \quad (III)$$

in which:
X and the index a are as defined;
R$_f$ is as defined, in which the optional pendent groups —CFYOR$_h$OH are substituted with optional pendent groups —COY,
A' is —COX with X as defined, or a group selected from —F, —Cl and —H, with the provisio that A' can be a group selected from —F, —Cl and —H only when a=1;
working with a ratio k $$k = \frac{\text{equivalents}-B \text{ of alkylating agent } (II)}{\text{equivalents}-COX + \text{equivalents}-COY \text{ of } (III)}$$

between 1 and 100, limits inclusive,
with the condition that K is between 1.25 and 100, limits inclusive, when A' is —F, —Cl or —H,
in the presence of a source of fluoride anions, to obtain a product of formula:

$$A''-(R_f)_a—CFX—O—R_hO—(CFX—(R_f)_a—CFX—O—R_hO—)_nH \quad (I)$$

in which:
R$_h$ is as defined above,
R$_f$ is as defined, in which the optional pendent groups —CFYOR$_h$OH are substituted with pendent groups —CFYOR$_h$OB in which Y and B are as defined,
A" is equal to —CFXOR$_h$OB when A' in formula (III) is —COX with X as defined, or is a group selected from —F, —Cl and —H, when A' in formula (III) is a group selected from —F, —Cl, and H;
n is as defined and with the condition that n=0 when A" is chosen from —F, —Cl and —H;

Step b)
hydrolysis or salification of the product of formula (IV) and production of the compounds of formula (I);

Step c)
recovery of the product of formula (I) obtained in step b).

Step a) is described in greater detail.

In the alkylating agent of formula (II) R' may be an aromatic that is optionally substituted, preferably with C$_1$-C$_6$ alkyl groups, which are linear or branched when possible. R' is preferably phenyl or tolyl.

As has been stated, the chain R$_f$ of compound (III) may contain pendent groups —COY in which Y=F or C$_1$-C$_6$ perfluoroalkyl, which are linear or branched when possible. At the end of step a), the groups —COY are converted into —CFYOR$_h$OB. At the end of step b), the groups —CFYOR$_h$OB, if present, are converted into groups —CFYOR$_h$OH.

Solvents are preferably used in this step, even more preferably polar aprotic solvents.

In step a), (II) may first be added to (III), or vice versa, or they may be added at the same time. Preferably, compound (III) is added to the source of fluoride ions. Next, compound (II) is added to the reaction mixture. One preferred procedure consists in adding compounds (II) and (III) with stirring.

The carbonyl reagent (III) may be a mono functional, difunctional or polyfunctional compound. The monofunctional compounds of formula (III) have functionality f=1. The term "functionality f" means the total number of groups —COX and of groups —COY per molecule of the compound of formula (III). In the difunctional compounds, f=2, and in the polyfunctional compounds, f is greater than or equal to 3.

The compound of formula (III) may also be used in the form of a mixture of the mono functional, difunctional and polyfunctional compounds as defined above. For example, if the compound is constituted by 50 mol % of monofunctional molecules and 50 mol % of difunctional molecules, the average functionality is 1.5.

The ratio k is preferably a value between 1.05 and 20 and even more preferably between 1.1 and 10, when difunctional compounds of formula (III) are used. In particular, when k is between 1 and 1.5, alcohols of formula (I) in which n is greater than 0 are obtained. When —COX groups are still present in the reaction product, it is preferable to add further amounts of difunctional alkylating agent (II) to obtain total conversion of the —COX.

When monofunctional compounds of formula (III) are used, k is preferably chosen between 2 and 100 and more preferably between 3 and 20.

When polyfunctional compounds of formula (III) are used, k is preferably chosen between 2 and 100 and more preferably between 3 and 20. In this way, the formation of crosslinked products is avoided.

Examples of sources of fluoride anions that may be mentioned include metal fluorides, for instance KF, RbF, CsF or AgF, optionally mixed together. The metal fluorides may be used in native form or supported, for example on charcoal, NaF or $CaF_2$. The amount of source of fluoride anions is generally between 0.01 and 10 times the sum of the equivalents of the groups —COX and —COY. It is preferable to use metal fluorides in an amount of between 1 and 3 times the sum of the equivalents of the groups —COX and —COY when B is R'—$SO_2$— in formula (II). By working under these conditions, high conversion rates are obtained, of even greater than 90%.

It is also possible to use organic fluorides as source of fluoride anions, for example fluorides of quaternary ammonium or of phosphonium salts, or complexes of the type such as pyridine-HF (Olah's reagent) or triethylamine-HF (see, for example, Y. Cherbukov, G. J. Lillquist, J. Fluor. Chem. 118 (2002) 123-126).

KF or CsF is preferably used as source of fluoride anions.

The reaction is preferably performed under anhydrous conditions. For example, the dehydration of the sources of inorganic fluoride anions my be performed by prolonged heating at high temperature (T>200° C.) under a stream of nitrogen or under vacuum. The dehydration of the solvents is performed via methods known in the art, for example by distillation or by treating with molecular sieves, for example.

The products of formula (III) may contain traces of HF. In this case, the reaction is preferably performed using acid acceptors or HF acceptors, for instance tertiary amines or sodium fluoride. The tertiary amines may be aliphatic or aromatic, preferably aliphatic. Mention may be made, for example, of triethylamine and tributylamine.

It is optionally possible to perform the reaction of phase a) in the presence of phase-transfer catalysts, for example crown ethers and cryptands, in order to increase the rate of reaction.

Toluene, xylene, etc. may be mentioned as solvents. Glyme, preferably diglyme, triglyme or tetraglyme; tetrahydrofuran, acetonitrile, dimethyl carbonate or dimethyl sulfoxide, and more preferably glyme, may be mentioned as polar aprotic solvents. It is optionally possible to use partially fluorinated cosolvents, for instance hydrofluoro polyethers, hydrofluoro ethers or hydrofluorocarbons. Commercially known hydrofluoropolyethers such as H-Galden® are preferred cosolvents.

The reaction temperature is generally between −50° C. and +200° C. and preferably between −40° C. and +150° C.

The choice of the temperature depends on the reactivity of the alkylating compound (II), in addition to the boiling point of the reaction mixture and the pressure. The higher the reactivity of the alkylating agent, the lower the reaction temperature. By working with very reactive alkylating compounds (II), for instance triflates (B=$CF_3SO_2$—), the reaction may advantageously be performed at room temperature or at lower temperatures.

By working with alkylating compounds (II) such as fluoroformates (B=FC(O)—), the reaction is preferably performed at temperatures of between 60 and 150° C.

In step a), the pressure is generally between 1 and 50 bar, preferably between 1 and 20 bar and more preferably 1-10 bar.

At the end of step a), and before performing step b), it is preferable to remove the solvent, the possible cosolvents and the excess alkylating agent via known techniques, for instance separation or distillation.

The compounds (III) in which $R_f$ is a monofunctional or difunctional perfluoropolyether are prepared, for example, as described in U.S. Pat. No. 3,847,978, US 2004/147 780, U.S. Pat. No. 3,242,218, US 2005/019 2413 A1 and WO 2007/075 804.

The compounds (III) in which $R_f$ is a polyfunctional perfluoropolyether may be prepared, for example, as described in U.S. Pat. No. 4,853,097.

The compounds (III) in which $R_f$ is perfluoroalkyl may be prepared, for example, as described in U.S. Pat. No. 2,519, 983 and U.S. Pat. No. 5,466,877.

The compounds (II) belonging to the class of alkyl fluoroformates (B=F—C(O)—) may be prepared, for example, by reaction between a hydrogenated diol of formula HO—$R_h$—OH, in which $R_h$ is as defined, with COFX', in which X'=F, Br, Cl, according, for example, to the procedures described in U.S. Pat. No. 3,362,980, or in P. E. Aldrich and W. A. Sheppard, J. Org. Chem. 29 (1964) 11-15.

The alkylating compounds (II) in which B is R'—$S(O)_2$— are generally commercially available, in particular as regards the classes of tosylates (B=$CH_3$—Ar—$SO_2$—, with Ar=phenyl) and of triflates (B=$CF_3SO_2$—).

These products may be synthesized, for example, by reacting a hydrogenated diol of formula HO—$R_h$—OH, with $R_h$ as defined above, with halides of the corresponding sulfonic acid of formula R'—$SO_2$—X' (X'=F, Cl, Br), in which R' is as defined above, according to the procedures reported in the literature in Vogel's, "Textbook of Practical Organic Chemistry"—4$^{th}$ Edition—Longman.

In step b), the compound of formula (IV) is converted into the hydrofluoro alcohol of formula (I) via a hydrolysis or salification reaction. The hydrolysis or salification reactions may be performed at temperatures of between 5° C. and 150° C., directly on the reaction mixture obtained in a), or on the reaction product of step a) after removal of the solvent and/or reagents and/or by-products, for example by distillation. The salification is performed using a base, for instance aqueous solutions of NaOH or KOH.

In step c), the product of formula (I) is recovered, for example by distillation or by separation. The product obtained may be subjected to purification, for example by washing. Preferably, the product obtained is passed through a bed of alumina.

As stated, the hydrofluoro alcohols of formula (I) of the present invention show improved chemical stability, in particular with respect to bases and Brönsted acids and Lewis acids, when compared with the hydrofluoro alcohols of the prior art, in combination with improved thermal stability at higher temperatures, of greater than 180° C., and even up to about 220° C.

The hydrofluoro alcohols of the present invention may be used in the treatment of surfaces for giving water- and/or oil-repellency properties. Examples of surfaces that may be mentioned include cardboard, glass, stone, wood, fabrics, etc.

The alcohols may be used as surfactants, for example in detergency, in the polymerization of hydrogenated, fluorinated monomers, preferably fluorinated monomers. In addition, they may be used as polymerization surfactants in the preparation of non-melt-processable (co)polymers, melt-processable polymers and elastomeric polymers. They may also be used as lubrication additives, for example for imparting rustproofing and anti-wear properties to the fluorinated lubricants in the form of oils or greases, preferably perfluoropolyether lubricants.

Another use of the alcohols of the present invention is as processing aids for hydrogenated and fluorinated polymers. They may also be used as additives for modifying the surface properties of hydrogenated and fluorinated polymers.

The alcohols of the invention may also be used as magnetic lubricants or as liquids for immersion microscopy, for example as described in U.S. Pat. No. 7,285,231.

In particular, the hydrofluoro polyether alcohols with functionality of 2 may be used as macromers (building blocks) for the synthesis of polymer materials with a low Tg. Polyfunctional alcohols may be used for crosslinking polymers.

The compounds of formula (I) of the invention may be dispersed or dissolved in environmentally friendly hydrogenated solvents, for instance ketones and ethers. This is particularly advantageous in the formation of coats.

The hydrofluoro alcohols of formula (I) of the present invention may be used as precursors in the preparation of derivatives having various types of functionality. Mention may be made of acetals, ketals, urethanes or esters, for instance carboxylic, phosphoric, boric, sulfonic or acrylate esters.

The esters obtained from the alcohols of the present invention show improved stability to hydrolysis when compared with those of the prior art.

Carboxylic esters may be obtained, for example, by reaction with carboxylic acids of formula RCOOH, in which R is a hydrogenated or fluorinated radical, for example $C_1$-$C_{20}$ alkyl. When R is hydrogenated, the reaction is preferably performed in the presence of acid or base catalysts and at temperatures of between 50 and 150° C. When R is perfluorinated, the use of catalysts is optional and the reaction is performed at room temperature.

Phosphoric esters may be obtained, for example, by reaction of phosphorus oxychloride $POCl_3$, or with pyrophosphoric acid $[O=P(O)(OH)_2]_2$.

Boric esters may be obtained, for example, by reaction with boric acid $H_3BO_3$, while heating at temperatures of about 100° C.

Sulfonic esters may be obtained, for example, by reaction with sulfonyl halides, for example p-toluenesulfonyl chloride and trifluoromethanesulfonyl fluoride at relatively low temperatures (0-20° C.). By reacting colour under the same conditions, the products of formula (I) with thionyl chloride, derivatives with chlorosulfite (—$SO_2Cl$) and —Cl end groups are obtained.

The acetals and ketals may be obtained, for example, by reaction with aldehydes and ketones, respectively, in the presence of Lewis acids or Brönsted acids as catalysts.

The urethanes may be obtained, for example, by reaction with isocyanates.

The acrylates may be obtained, for example, by reaction with acryloyl chloride or methacryloyl chloride at a temperature of between room temperature and the reflux point of the mixture.

The reactions reported above are described, for example, in C. Tonelli et al., Journal of Fluorine Chemistry, 95 (1999) 51-70, and March's Advanced Organic Chemistry, Fifth Edition, Wiley-Interscience Publication, 2005.

A further subject of the present invention is hydrofluoropolyethers that may be obtained from hydrofluoro alcohols of formula (I), having the formula (V):

$$A_1\text{-}(R_f)_a\text{—CFX—O}[R_hO\text{—(CFX—}(R_f)_{a^*}\text{—CFX—} O\text{—}R_hO\text{—})_{n-1}\text{—CFX—}(R_f)_{a^*}\text{—CFX—O}]_w\text{—} CH_2\text{-}D_q\text{-}(T)_{k^\circ}$$

in which:
$A_1$ is selected from:
  a group of formula: —CFX—O—$CH_2$-$D_q$-$(T)_{k^\circ}$; and
  a group selected from —F, —Cl or —H,
with the provisio that A can be a group selected from —F, —Cl and —H only when a=1;

a and a*, equal to or different from each other and at each occurrence, are independently an integer equal to 0 or 1,
n, X, $R_h$ are as defined,
w is an integer and is 0 when n=0; is 1 when n≥1,
$R_f$ is as defined, in which the optional pendent groups —CFY—$OR_h$OH are substituted with pendent groups —CFYO—$CH_2$-$D_q$-Mie,
D is a bridge for connection between the —$CH_2$— group and the end group T,
T represents one or more functional groups,
k° is an integer from 1 to 4, preferably 1-2,
q is an integer equal to 0 or 1, The compounds of formula (V) may be prepared, for example, according to the methods described in U.S. Pat. No. 3,810,874, U.S. Pat. No. 4,721,795 and U.S. Pat. No. 4,757,145.

D is a divalent radical, preferably a linear aliphatic group —$(CH_2)_{m'}$—, in which m' is an integer from 1 to 9, or an (alkenyl)cycloaliphatic or (alkenyl)aromatic group. D may optionally contain heteroatoms in the alkenyl chain or in the ring. Optionally, D may contain amide, imine, ester or sulfide groups.

The number of carbon atoms in the cycloaliphatic groups ranges from 3 to 9, and that in the aromatic groups ranges from 6 to 19; the group D may also be optionally formed by combining aliphatic, cycloaliphatic and aromatic groups as defined above.

The group D may also be, for example: —$CONR_a$—, in which $R_a$ has the following meanings: H, $C_1$-$C_{15}$ alkyl group, $C_3$-$C_{15}$ cycloaliphatic group or $C_5$-$C_{15}$ aromatic group; —$CO_2$—; —COS—; —CO—; a heteroatom, triazine groups, aromatic heterocycles with a 5- or 6-atom ring, preferably containing two or more identical or different heteroatoms.

When compound (V) has functionality equal to 2, it may be obtained, for example, with k°=1 and $A_1$ is —CFX—O—$CH_2$-$D_q$-$(T)_k$.

The hydrofluoropolyethers of formula (V) are used as macromers for producing polymers by polycondensation or polyaddition reactions.

When T is a reactive functional end group and k°>1, the perfluoropolyethers of formula (V) are used as macromers for producing, for example, star polymers, via polycondensation or polyaddition reactions, with improved mechanical properties.

The compounds of formula (V) containing reactive functional end groups T may be used for treating surfaces of natural and artificial substrates; mention may be made of cardboard, cotton, wood, stone materials, polymer materials and metal substrates.

When T is an unreactive functional end group, the compounds of formula (V) are used as lubricants with improved surface adhesion properties.

In particular, T may be, for example: —SH, —SR″, —$NR_2$″, —COOH, —$SiR''_dQ_{3-d}$ in which Q is a group OR″, d is an integer between 0 and 3, R″ is an alkyl, cycloaliphatic or aromatic group, R‴ optionally contains fluoro; —CN, —NCO, —CH=$CH_2$,

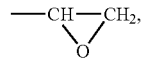

—COR″, —$OSO_2CF_3$, —OCOCl, —OCN, —N(R″)CN, —(O)COC(O)—, —I, —CHO, —CO, —CH(—$OCH_3$)$_2$, —$SO_2Cl$, —C($OCH_3$)=NH, —C($NH_2$)=NH, —CH(O—

H)CH$_2$—OH, —CH(—COOH)$_2$, —CH(—C—OOR")$_2$, —CH(CH2OH)$_2$, —CH(CH$_2$—NH$_2$)$_2$, —CH(CN)$_2$, —CH(CH$_2$O—CH$_2$—CH=CH$_2$)$_2$, an aromatic radical substituted with a methylenedioxy group:

The compounds of formula (V) are prepared from the compounds of formula (I) via known reactions, for example using the reagents and the reaction conditions described, for example, in U.S. Pat. No. 3,810,874 and U.S. Pat. No. 6,127,498.

A number of non-limiting examples illustrating the present invention are given hereinbelow.

EXAMPLE 1

Preparation of the Alkylating Agent FC(O)O(CH$_2$)$_4$OC(O)F of Formula (II)

According to the teaching reported in P. E. Aldrich and W. A. Sheppard, J. Org. Chem. 29 (1964) 11-15, the alkylating compound (II) FC(O)O(CH$_2$)$_4$OC(O)F is prepared from 1,4-butanediol.

EXAMPLE 2

Preparation of an Alcohol of Formula (I) with n=0 from the Alkylating Agent (II) FC(O)O(CH$_2$)$_4$OC(O)F Obtained in Example 1

Step a)

1.6 g of anhydrous CsF (10.5 mmol), 15.0 g of diglyme and 2.0 g (4.4 mmol) of a carbonyl perfluoropolyether (III) prepared according to the teaching of patent application US 2005/0192413 and having the following structure (III):

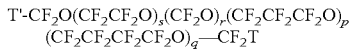
(CF$_2$CF$_2$CF$_2$CF$_2$O)$_q$—CF$_2$T in which T and T' are both —COF; s=1.91, r=0.34, p=0.002 and q=0.005, number-average molecular weight equal to 455, are placed in a glass 50 ml three-necked round-bottomed flask, inside a dry box.

The mixture is stirred at room temperature for 60 minutes in order to convert the acyl fluoride end groups into the respective alkoxy anions.

5.5 g (30 mmol) of alkylating agent (II) FC(O)O(CH$_2$)$_4$OC(O)F are then added.

The ratio k between the equivalents of alkylating agent (II) and the equivalents of carbonyl compound (III) is equal to 6.8.

The mixture is gradually heated to 110° C. and maintained at this temperature for 48 hours.

$^{19}$F NMR analysis of the reaction mixture indicates a 95 mol % conversion of the —COF end groups of the perfluoropolyether (III) into —CF$_2$O(CH$_2$)$_4$OC(O)F groups of the compound (IV).

By distillation under vacuum, the diglyme and the unreacted butanediol formate FC(O)O(CH$_2$)$_4$OC(O)F (II) are recovered.

Step B)

The distillation residue is transferred into a polyethylene container and washed several times with water in order to convert all the end groups —O(CH$_2$)$_4$O—COF into —O(CH$_2$)$_4$—OH.

Step C)

The fluorinated phase is separated out, recovered, diluted with 15 g of H-Galden® ZV60 and purified with 3 g of alumina.

The solution is filtered and the solvent evaporated off to give 1.4 g of product, which, by $^{19}$F NMR and $^1$H NMR analysis, is found to be constituted of the compound of structure (I) having the formula:

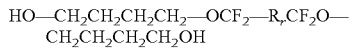
CH$_2$CH$_2$CH$_2$CH$_2$OH in which R$_f$ is —CF$_2$O—(CF$_2$CF$_2$O)$_s$(CF$_2$O)$_r$(CF$_2$CF$_2$CF$_2$O)$_p$(CF$_2$CF$_2$CF$_2$CF$_2$O)$_q$CF$_2$—, s=1.90, r=0.32, p=0.002 and q=0.005, the number-average molecular weight of product (I) obtained is 635.

EXAMPLE 3

Preparation of an Alcohol with n>0 of Formula (I) Starting with FC(O)O(CH$_2$)$_4$OC(O)F Example 2 is repeated, but using in step a) 5.0 g of anhydrous CsF (32.9 mmol), 6.9 g (15.1 mmol) of carbonyl perfluoropolyether (III) and 2.88 g (15.8 mmol) of butanediol formate FC(O)O(CH$_2$)$_4$OC(O)F.

The value of k is equal to 1.05.

The mixture is gradually heated to 110° C. and maintained at this temperature for 100 hours.

$^{19}$F NMR analysis of the product obtained indicates the presence of a polymeric product with a 90 mol % conversion of the —COF end groups of the perfluoropolyether (III).

2.75 g (15 mmol) of FC(O)O(CH$_2$)$_4$OC(O)F in diglyme are added to the reaction mixture. After reaction for 100 hours at 110° C., the conversion is equal to 98 mol %.

Step c) of Example 2 is repeated, but the fluorinated phase is diluted with 50 g of Galden® HT55 and is purified with 8 g of alumina. 6.0 g of product are obtained, which, by $^{19}$F NMR and $^1$H NMR analysis, are found to be constituted by the compound of structure (I) having the formula:

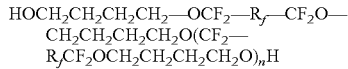

R$_f$ is —CF$_2$O—(CF$_2$CF$_2$O)S(CF$_2$O)$_r$(CF$_2$CF$_2$CF$_2$O)$_p$(CF$_2$CF$_2$CF$_2$CF$_2$O)$_q$CF$_2$—, s=1.91, r=0.35, p=0.004, q=0.005, n=7.4, the number-average molecular weight is 4700. The product is a highly viscous liquid polymer.

The data of Examples 2 and 3 show that by varying the ratio k, it is possible to control the value of n.

EXAMPLE 4

Preparation of the Alkylating Agent (II) FC(O)OCH$_2$-(cC$_6$H$_{10}$)—CH$_2$OC(O)F According to the teaching reported in P. E. Aldrich and W. A. Sheppard, J. Org. Chem. 29 (1964) 11-15, the alkylating compound (II) FC(O)OCH$_2$-(cC$_6$H$_{10}$)—CH$_2$OC(O)F is prepared from 1,4-cyclohexanedimethanol.

EXAMPLE 5

Preparation of an Alcohol of Formula (I) Having n=0, Starting with FC(O)OCH$_2$-(cC$_6$H$_{10}$)—CH$_2$OC(O)F (II) Obtained in Example 4

Example 2 is repeated, but using in step a) 1.5 g of anhydrous CsF (9.9 mmol), 1.5 g (3.3 mmol) of the carbonyl perfluoropolyether (III) and 4.1 g (17 mmol) of the alkylating agent (II) FC(O)OCH$_2$-(cC$_6$H$_{10}$)—CH$_2$OC(O)F prepared in Example 4.

The value of k is equal to 5.2.

The mixture is gradually heated to 110° C. and maintained at this temperature for 100 hours.

In step b), the end groups —R$_h$—OCOF are hydrolysed.

At the end of step c), 1.2 g of product are obtained, which, by $^{19}$F NMR and $^1$H NMR analysis, have the structure (I) having the formula:

HOCH$_2$-(cC$_6$H$_{10}$)—CH$_2$—OCF$_2$—R$_f$—CF$_2$O—CH$_2$-(cC$_6$H$_{10}$)—CH$_2$OH in which R$_f$ is —CF$_2$O—CF$_2$CF$_2$O)$_s$(CF$_2$O)$_r$(CF$_2$CF$_2$CF$_2$O)$_p$(CF$_2$CF$_2$CF$_2$CF$_2$O)$_q$CF$_2$—, s=1.88, r=0.34, p=0.001 and q=0.004; the number-average molecular weight of product (I) is 747.

EXAMPLE 6

Preparation of an Alcohol of Formula (I) Having n=0, Starting with Ethylene Glycol Tosylate (II)

Example 2 is repeated, but using in step a) a glass 1-liter three-necked round-bottomed flask, 21 g of anhydrous CsF (138 mmol), 600 g of diglyme, 27 g (36 mmol) of a carbonyl perfluoropolyether (III) with s=3.64, r=1.54, p=0.015 and q=0.018, number-average molecular weight equal to 740, and 200 g (540 mmol) of ethylene glycol tosylate (Aldrich) as alkylating agent (II).

k is equal to 15.9.

The mixture is gradually heated to 60° C. and maintained at this temperature for 200 hours.

$^{19}$F NMR analysis of the reaction mixture indicates a 99 mol % conversion of the —COF end groups of the perfluoropolyether compound (III).

Step b) of Example 2 is repeated, but using 250 ml of aqueous KOH solution at 20% by weight for washing.

Step c)

The mixture is heated at 90° C. with stirring for one hour. The stirring is stopped and the mixture is maintained at 90° C., and the fluorinated phase that separates out is removed with a syringe. The product obtained is treated with aqueous KOH of step b), this treatment being repeated three times. The product is then washed with distilled water.

20 g of a fluorinated compound are recovered in the form of a viscous oil of formula (I):

HO—(CH$_2$)$_2$—OCF$_2$—R$_f$CF$_2$O—(CH$_2$)$_2$OH in which R$_f$ is —CF$_2$O—(CF$_2$CF$_2$O)$_s$(CF$_2$O)$_r$(CF$_2$CF$_2$CF$_2$O)$_p$(CF$_2$CF$_2$CF$_2$CF$_2$O)$_q$CF$_2$—, s=3.66, r=1.54, p=0.015, q=0.017, the average molecular weight is 870.

EXAMPLE 7

Preparation of an Alcohol of Formula (I) Having n=0, Starting with Propanediol Tosylate (II)

Example 6 is repeated, but using in step a) a 50 ml three-necked round-bottomed flask, 1.5 g (9.9 mmol) of anhydrous CsF for the heat treatment, under a stream of nitrogen, at 350-370° C. for 4 hours, 24 g of tetraglyme and 2.0 g (2.7 mmol) of the perfluoropolyether (III) and 14.0 g (36 mmol) of 1,3-propanediol di-p-tosylate (TsO—CH$_2$CH$_2$CH$_2$—OTs) from Aldrich.

The value of k is 13.3.

The mixture is gradually heated to 100° C. and maintained at this temperature for 20 hours.

$^{19}$F NMR analysis of the reaction mixture indicates a greater than 99 mol % conversion of the —COF end groups of the perfluoropolyether compound (III).

In step b), 40 ml of aqueous KOH solution at 20% by weight are used.

After step c), 1.0 g of a compound is obtained in the form of a viscous oil of structure (I) having the formula:

HO—CH$_2$CH$_2$CH$_2$—OCF$_2$—R$_f$—CF$_2$O—CH$_2$CH$_2$CH$_2$OH in which R$_f$ is —CF$_2$O—(CF$_2$CF$_2$O)$_s$(CF$_2$O)$_r$(CF$_2$CF$_2$CF$_2$O)$_p$(CF$_2$CF$_2$CF$_2$CF$_2$O)$_q$CF$_2$—, s=3.62, r=1.50, p=0.015, q=0.018, the number-average molecular weight is 900.

EXAMPLE 8

Preparation of an Alcohol (I) with n>0 from Propanediol Tosylate (II)

Example 6 is repeated, but using in step a) a 50 ml three-necked round-bottomed flask, 1.5 g (9.9 mmol) of anhydrous CsF for the heat treatment, under a stream of nitrogen, at 350-370° C. for 4 hours, 12 g of tetraglyme, 2.0 g (2.7 mmol) of the perfluoropolyether (III) and 1.15 g (3.0 mmol) of 1,3-propanediol di-p-tosylate (TsO—CH$_2$CH$_2$CH$_2$—OTs) from Aldrich.

The value of k is 1.1.

The mixture is gradually heated to 100° C. and maintained at this temperature for 20 hours. 4 g of 1,3-propanediol di-p-tosylate (10.4 mmol) are then added. The mixture is stirred at 100° C. for 50 hours.

$^{19}$F NMR analysis of the reaction mixture indicates a 99 mol % conversion of the —COF end groups of the perfluoropolyether compound (III).

After step c), 1.8 g of a compound is obtained in the form of a viscous oil of structure (I) having the formula:

HO—CH$_2$CH$_2$CH$_2$—OCF$_2$—R$_f$—CF$_2$O—
CH$_2$CH$_2$CH$_2$O—(CF$_2$—R$_f$—CF$_2$O—
CH$_2$CH$_2$CH$_2$O)$_n$—H in which R$_f$ is —CF$_2$O—(CF$_2$CF$_2$O)s(CF$_2$O)r(CF$_2$CF$_2$CF$_2$O)$_p$(CF$_2$CF$_2$CF$_2$CF$_2$O)$_q$CF$_2$—, s=3.62, r=1.59, p=0.011, q=0.014, n=6.4, the number-average molecular weight is 6100.

EXAMPLE 9

Preparation of a Monofunctional Perfluoroalkyl Alcohol (I)

24 g of anhydrous CsF (155 mmol), 675 g of diglyme and 225 g (610 mmol) of ethylene glycol tosylate (Aldrich) are placed in a 1-liter steel autoclave, inside a dry box. Next, by condensation at −10° C., 22.5 g (103 mmol) of heptafluorobutyryl fluoride CF$_3$CF$_2$CF$_2$COF (Bp=8° C.), supplied by ABCR, are introduced.

The value of k is equal to 5.9.

The mixture is stirred at room temperature for 10 hours, then heated at 40° C. for 40 hours, and then heated at 60° C. for 40 hours.

The reaction mixture is discharged and distilled under vacuum. 250 ml of aqueous KOH solution at 20% by weight are added to the distillation residue. The mixture is distilled and the distillate subjected to rectification.

13.5 g of product of formula:

CF$_3$CF$_2$CF$_2$CF$_2$OCH$_2$CH$_2$OH are obtained.

Application Tests

EXAMPLE 10

Acid Stability Test 12 meq. of the product obtained in Example 6 are placed in a glass 25 ml round-bottomed flask. 10 g of aqueous HI at 20% by weight (16 mmol) are added with stirring, and the solution is gradually heated to a temperature of 100° C.

Every three hours, samples are taken for $^{19}$F NMR analysis-2-3 drops of sample diluted with about 1.5 ml of deuterated acetone.

No variation in the $^{19}$F NMR spectrum, relative to that of the initial sample, is observed after 12 hours. Thus, the compound does not undergo degradation.

EXAMPLE 11

Example 10 was repeated, but using the product of Example 9. The compound does not undergo degradation.

COMPARATIVE EXAMPLE 12

The alcohol $CF_3CF_2CF_2CH_2OH$ (b.p. 96-97° C.) from Aldrich is converted into the monofunctional alcohol of formula:

$CF_3CF_2CF_2CH_2$—O—$(CH_2CH_2O)_{sa}H$ by reaction with ethylene oxide, according to the following procedure.

An amount of t-BuOK equal to 0.11 g (1 mmol) is added to 4.0 g (20 mmol) of $CF_3CF_2CF_2CH_2OH$ at a temperature of 50° C. in a steel reactor. 1.15 g (26 mmol) of ethylene oxide are added, with very slow stirring. After 16 hours, the reaction mixture is cooled to room temperature, discharged and acidified with aqueous HCl solution at 10% by weight. After filtration, 4.6 g of fluorinated phase are separated out.

By $^{19}$F NMR analysis, the compound of the separated phase has the formula:

$CF_3CF_2CF_2CH_2$—O—$(CH_2CH_2O)_{sa}H$ sa=1.2.

The compound is formed from a mixture of two isomers having the formulae:

$CF_3CF_2CF_2CH_2$—O—$(CH_2CH_2O)_{sa}H$ with sa=1
83%

$CF_3CF_2CF_2CH_2$—O—$(CH_2CH_2O)_{sa}H$ with sa=2
17%

Acid Stability Test

The mixture obtained is subjected to the acid stability test under the conditions indicated in Example 10.

After reaction for 3 hours, the compound $CF_3CF_2CF_2CH_2$—O—$(CH_2CH_2O)_2H$ is degraded, since all the ether bonds —$CH_2CH_2O$—$CH_2CH_2$— have reacted.

After reaction for 12 hours, decomposition of 4% of the ether bonds of the compound $CF_3CF_2CF_2CH_2$—O—$(CH_2CH_2O)_1H$ is observed.

The results obtained in Comparative Example 12, compared with those of Examples 10 and 11, show that the hydrofluoro alcohols of the invention have improved acid stability with respect to the comparative alcohol.

EXAMPLE 13

Heat Stability Test 5.2 g (12 meq.) of the hydrofluoro alcohol obtained in Example 6 are introduced, under a nitrogen atmosphere in a dry box, into a 25 ml AISI 316 Swagelok steel bomb. The bomb is heated at a temperature of 220° C. for ten hours.

At the end of the test, the $^{19}$F NMR and $^1$H NMR spectra of the product are identical to the initial spectra of the starting sample. Thus, the product has not undergone any degradation following the heat treatment.

EXAMPLE 14

Example 13 is repeated, but using the hydrofluoro alcohol obtained in Example 9.

The product has not undergone any degradation following the heat treatment.

COMPARATIVE EXAMPLE 15

Example 12 is repeated, but using the hydrofluoro alcohol $CF_3CF_2CF_2CF_2CH_2CH_2OH$ from Aldrich.

The $^{19}$F NMR spectrum of the product obtained indicates and approximately 7 mol % degradation of the hydrofluoro alcohol. The $^{19}$F NMR and $^1$H NMR analyses reveal as main degradation product $CF_3CF_2CF_2CF$=$CHCH_2OH$, which indicates dehydrofluorination.

The results of Comparative Example 15, relative to those obtained in Examples 13 and 14, show that the hydrofluoro alcohols of the present invention are more thermally stable.

EXAMPLE 16

Base Stability Test 8.2 g (19 meq) of the hydrofluoro alcohol obtained in Example 6 are placed in a glass round-bottomed flask, into which are added 15 g of aqueous KOH solution at 10% by weight (27 mmol of KOH). The mixture is heated at 90° C. for 10 hours.

$^{19}$F NMR and $^1$H NMR analysis of the reaction mixture does not reveal any degradation of the hydrofluoro alcohol.

EXAMPLE 17

Example 16 is repeated, but using the hydrofluoro alcohol obtained in Example 9.

The NMR analysis does not reveal any degradation of the hydrofluoro alcohol.

COMPARATIVE EXAMPLE 18

Example 16 is repeated, but using the hydrofluoro alcohol $CF_3CF_2CF_2CF_2CH_2CH_2OH$ from Aldrich.

The NMR spectrum indicates approximately 10 mol % degradation of the hydrofluoro alcohol. The main degradation product is:

$CF_3CF_2CF_2CF$=$CHCH_2OH$.

The results of Comparative Example 18, relative to those of Examples 16 and 17, show that the hydrofluoro alcohols of the present invention are more stable to bases than the comparative alcohol of Example 18.

The invention claimed is:
1. A hydrofluoro alcohol of formula:

$$A-(R_f)_a-CFX-O-R_hO-(CFX-(R_f)_{a^*}-CFX-O-R_hO-)_nH \quad (I)$$

wherein:

$R_h$ is a divalent $C_1$-$C_{20}$ hydrocarbon-based residue,

X is F or a $C_1$-$C_6$ (per)fluoroalkyl, which is linear or branched where possible, optionally containing one or more heteroatoms, a and a* are equal to 1, $R_f$ is a (per)fluoro(poly)oxyalkylene (PFPE) chain comprising one or more of the following units distributed along the chain: —($C_3F_6O$)—, —($CF_2O$)—, —($CF_2CF_2O$)—, —($CF_2CF_2CF_2O$)—, —($CF_2CF_2CF_2CF_2O$)—, or —($CF(CF_3)O$)—, optionally comprising one or more of the following units: —($CF_2CF(CFYOR_hOH)O$)—, —($CF(CFYOR_hOH)CF_2O$)—, or —($CF(CFYOR_hOH)O$)— with Y being F or a $C_1$-$C_6$ (per)fluoroalkyl, which is linear or branched where possible, A is:
- a group of formula: HO—$R_h$—O—CFX— in which $R_h$ and X have the same meaning as defined above, or
- a group selected from the group consisting of —F, —Cl, and —H;
- n is an integer from 0 to 200, with the condition that n=0 when A is selected from the group consisting of —F, —Cl, and —H.

2. The hydrofluoro alcohol according to claim 1, wherein $R_h$ is selected from the group consisting of:
- a $C_1$-$C_{10}$ alkyl chain, which is linear or branched where possible,
- a $C_3$-$C_{10}$ cyclic ring or a $C_4$-$C_{20}$ alkyl chain comprising one or more $C_3$-$C_{10}$ cyclic rings, and
- an aromatic ring in which, optionally, one or more carbon atoms of said aromatic ring are substituted with a heteroatom, or a $C_6$-$C_{20}$ alkyl chain comprising one or more of said aromatic rings,
  wherein $R_h$ may contain one or more unsaturations; and wherein the cyclic and/or aromatic rings optionally have one or more hydrogen atoms replaced with $C_1$-$C_{10}$ (fluoro)alkyl chains, which are linear or branched where possible.

3. The hydrofluoro alcohol according to claim 1, wherein n ranges from 0 to 100.

4. The hydrofluoro alcohol according to claim 1, wherein $R_f$ is a PFPE chain with a number-average molecular weight from about 100 to about 10 000.

5. The hydrofluoro alcohol according to claim 1, wherein $R_f$ is selected from the group consisting of following structures:

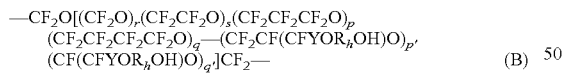

wherein the indices r, s, p, q, p' and q' are integers, including 0, such that the number-average molecular weight is from about 100 to about 10,000;

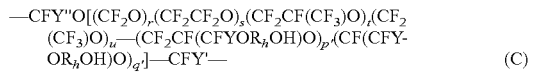

wherein the indices r, s, t, u, p' and q' are integers, including zero, such that the number-average molecular weight is from about 100 to about 10,000;

wherein Y, Y' and Y" are independently selected from the group consisting of F and $C_1$-$C_6$ (per)fluoroalkyl, which is linear or branched where possible.

6. A process for preparing the hydrofluoro alcohol of claim 1, comprising the following steps:

Step a)
reaction of a difunctional alkylating compound of formula:

wherein B is FC(O)—, or R'—$SO_2$— in which R' is an aromatic group, a hydrogenated or (per)fluorinated $C_1$-$C_{10}$ alkyl, which is linear or branched where possible, and $R_h$ is the same as defined in claim 1, with a carbonyl compound of formula:

wherein, in $R_f$, the optional pendent groups —$CFYOR_hOH$ are substituted with optional pendent groups —COY, with Y being F or a $C_1$-$C_6$ (per)fluoroalkyl, which is linear or branched where possible, X, $R_f$ and the index a have the same meaning as defined in claim 1, A' is —COX with X having the same meaning as defined in claim 1, or a group selected from the group consisting of —F, —Cl, and —H, with the proviso that A' is a group selected from the group consisting of —F, —Cl, and —H only when a=1, working with a ratio k:

$$k = \frac{\text{equivalents}-B \text{ of alkylating agent }(II)}{\text{equivalents}-COX + \text{equivalents}-COY \text{ of }(III)}$$

of between 1 and 100, limits inclusive, with the condition that k is between 1.25 and 100, limits inclusive, when A' is F, Cl or H, in the presence of a source of fluoride anions, to obtain a product of formula:

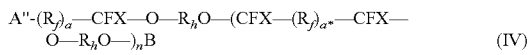

wherein, in $R_f$, the optional pendent groups —$CFYOR_hOH$ are substituted with optional pendent groups —$CFYOR_hOB$, A" is equal to —$CFXOR_hOB$ when A' in formula (III) is —COX with X having the same meaning as defined in claim 1, or A" is a group selected from the group consisting of —F, —Cl, and —H, when A' in formula (III) is a group selected from the group consisting of —F, —Cl, and H, n has the same meaning as defined in claim 1, and with the condition that n=0 when A" is selected from the group consisting of —F, —Cl, and —H;

Step b)
hydrolysis or salification of the product of formula (IV) and production of the compounds of formula (I); and Step c)
recovery of the product of formula (I).

7. The process according to claim 6, wherein, in the alkylating agent of formula (II), R' is an aromatic, optionally substituted with C1-C6 alkyl groups, which are linear or branched where possible.

8. The process according to claim 6, wherein, in step a), k is between 1.05 and 20 when difunctional compounds of formula (III) are used; or k is between 2 and 100 when monofunctional or polyfunctional compounds of formula (III) are used.

9. The process according to claim 6, wherein the source of fluoride anions is selected from the group consisting of metal fluorides, optionally supported; and organic fluorides.

* * * * *